United States Patent [19]

Wiktor

[11] Patent Number: 4,649,922

[45] Date of Patent: Mar. 17, 1987

[54] CATHETER ARRANGEMENT HAVING A VARIABLE DIAMETER TIP AND SPRING PROSTHESIS

[76] Inventor: Donimik M. Wiktor, 4 Culin Dr., Cranford, N.J. 07016

[21] Appl. No.: 821,800

[22] Filed: Jan. 23, 1986

[51] Int. Cl.⁴ .............................................. A61M 29/02
[52] U.S. Cl. .................. 128/344; 128/348.1; 623/1
[58] Field of Search ............ 128/344, 345, 341, 348.1, 128/325; 623/1

[56] References Cited

U.S. PATENT DOCUMENTS 4,503,569  3/1985  Dotter .................. 128/303 R X
4,553,545 11/1985  Maass et al. ...................... 128/341
4,580,568  4/1986  Gianturco ..................... 128/345

Primary Examiner—Michael H. Thaler

[57] ABSTRACT

A catheter arrangement including an inflatable variable diameter element and a linearly expandable spring-like liner retained in a compressed state behind the inflatable element and means to change the diameter of the inflatable element. The expandable liner is transported to desired location in its compressed state and is released and allowed to expand after a successful P.T.A.P. operation when the balloon is deflated and evacuated creating a diameter of the balloon which is smaller than that of the expandable liner. The catheter is than allowed to be removed and withdrawn leaving the liner deployed and implanted within the blood vessel.

2 Claims, 4 Drawing Figures

CATHETER ARRANGEMENT HAVING A VARIABLE DIAMETER TIP AND SPRING PROSTHESIS

FIELD OF INVENTION

This invention relates to catheters in general and in particular to inflatable balloon-type catheters designed to open up clogged or otherwise obstructed arteries such as coronary arteries by means of the inflatable variable diameter tip being part of such catheter. More specifically, this invention relates to such catheter-type medical implements used for recanalization and having means to prevent restenosis after a successful percutaneous transluminar angio-plasty operation.

The following U.S. Patents are sited for reference: U.S. Pat Nos. 4,195,637 3,837,347 and 3,978,863.

DESCRIPTION OF PRIOR ART

Catheters as such are not new to the medical practitioners, they are frequently employed in internal medicine for such purposes as introduction of medications, diagnostics, recannalization and many other well known and useful purposes. Several techniques of recannalization and dilatation are known and have been used with various degrees of success. U.S. Pat. No. 4,195,637 describes in detail one particular technique where a catheter arrangement using an inflatable balloon at its distal end for purposes of opening an artery clogged with plaque is inserted into the afflicted area, where the balloon is subsequently inflated compressing said plaque, thus reopening the artery for a free flow of blood.

Other catheters are used primarily for diagnostic purposes where a radio-opaque dye is introduced through such catheter and with the aid of X-ray or a flouroscope the anatomical characteristics of the suspected area can be studied.

Several different methods of guidance for such catheters are known and discussed in details such as U.S. Pat. No. 4,033,331 and 3,528,406 and many others.

SUMMARY OF INVENTION

The catheter and the method of its use of this invention expands greatly the usefulness of this medical tool in that in addition to its normally intended function namely opening up of clogged arteries, it also assures, that once an opening has been established, the introduction and the deployment of the proper liner will maintain such re-opened vessel open without a possibility of reclosure after the catheter has been removed.

This method using the herein described innovation and improvement of presently known catheter as disclosed in Gruntzig U.S. Pat. No. 4,195,637 will forever remove the present factor of uncertainty such as: Will the artery again reclose and when? Or, will a surgery still be required and when?

The method and the extended use of it as described and depicted herein shows how the present catheter of the Gruntzig type or a similar one can be modified and improved upon to serve a dual purpose and enhance its usefulness and acceptance level manyfold.

The present catheter as disclosed in Gruntzig U.S. Pat No. 4,195,637 employs an inflatable element which is intended to be advanced to desired location in its deflated and collapsed state of minimal frontal area thus facilitating manipulation and easy entry to the desired location.

One of several objects of my invention is to add an expandable element basically tubular in nature immediately behind the balloon-type dilatation element, said expandable element being retained in its compressed state by the normal diameter of that dilatation element and without increasing the frontal area.

The primary object of this invention is to provide a new and improved construction of a catheter which enables a true recannalization of an occluded or partially obliterated blood vessel, which in addition to providing means for initially opening up an obstruction, will also provide an implantable element to be transported by the same catheter and which also will provide means for deployment of said implantable element immediately after an opening has been established and before the catheter has been completely removed. The dilatation balloon type element is intended as claimed in the aforementioned Patent to enter the desired area and be inflated thereby compressing the obstructing material against the walls of the afflicted vessel thus providing an improved and enlarged opening. My invention as described herein, will assure that by deploying the expandable element immediately after such an opening has been secured will indeed maintain such a newly created opening indefinitely.

The expandable element as shown herein basically consists of a stainless steel spring of the compression type with closed ends and possibly covered with a thin flexible membrane skin which in its natural state provides a tubular flexible liner which is quite rigid in its radial orientation. This expandable liner is in its compressed state retained between the back end of the inflatable element and a tapered ring provided for that purpose on the outside of the support hose located in close proximity behind the inflatable element, and is released by complete evacuation of the inflatable element immediately after proper dilatation has been completed.

Complete evacuation of said inflatable element creates a diameter which is less than that of the normal deflated state, this condition allows the spring to expand and to assume its normal state which is approximately four times the length of the compressed state.

It is yet another object of this invention to provide a simple balloon type catheter whose entire purpose and function is to facilitate transportation and deployment of a flexible liner inside a blood vessel such as the coronary artery before a stenosis sets in. The object here being, that the liner such as a helical open wound type spring made of stainless steel or gold be deployed as a prophilaxis to ward off an obstruction or occlusion within the artery thus preventing a possible heart attack.

The flexible liner of this helical open wound type spring is naturally flexible enough to resist fatigue induced stresses and possible breakage due to some flexing with every heartbeat, yet in its radial orientation is strong enough to resist collapsing due to possible build-up of plaque, thus maintaining a free opening for a free flow of blood. The open winding of the spring as deployed for example inside the left main coronary artery will allow sufficient amounts of blood to flow into its smaller branches between windings of that spring. It is hoped, that a simple spring as discussed above will offer enough protection from stenosis and that plaque build-up will not penetrate between spring windings, otherwise additional membrane-type cover for the spring might be required.

This preventive method of adding a flexible liner to a healthy artery might provide a better and lower risk and less expensive alternative to angio plasty.

DESCRIPTION OF INVENTION

For purposes of better understanding the basic embodiments of this invention reference is being offered to the following drawings where:

Figure 1:
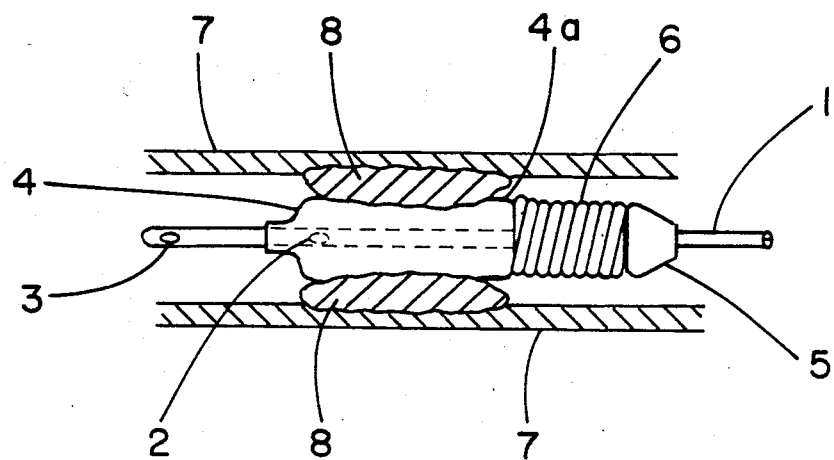
FIG. 1 is a partial cross sectional view of the distal end of a typical catheter of the balloon type where the inflatable element is in its normal state and the expandable member is retained in the compressed state by the balloon prior to deployment inside a blood vessel.
Figure 2:
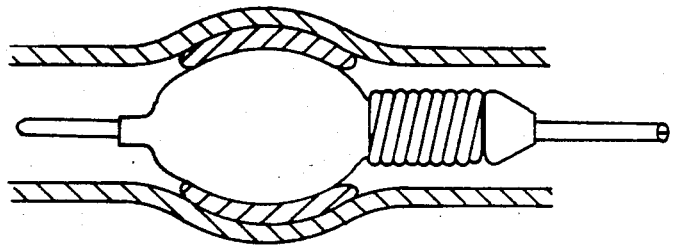
FIG. 2 shows the same device inside the afflicted blood vessel with the inflatable element fully inflated compressing the occluding plaque against the inside wall of the blood vessel; expandable member still compressed.
Figure 3:
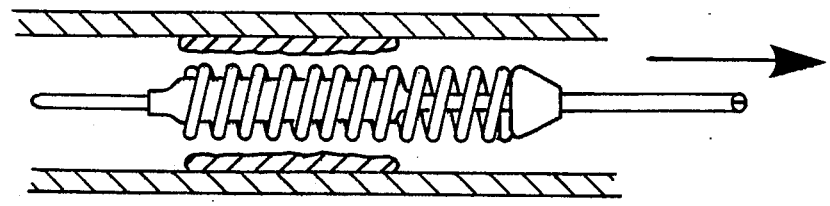
FIG. 3 shows plaque compressed, inflatable element deflated AMD evacuated creating a diameter of the balloon smaller then that of the expandable spring type liner, thus the spring type liner fully expanded, deployed and implanted and catheter being withdrawn.

In FIG. 1 the outside support hose 1 basically consists of a double lumen element, one lumen having an opening 2 inside the dilatation balloon 4, the other lumen within the same hose 1 has an opening 3 in front of the balloon 4. Opening 2 inside balloon 4 is used for a suitable fluid to enter inside the balloon and inflate it to a larger diameter as shown in FIG. 2. A collar 5 is fastened to outside of the hose 1 within close proximity and behind balloon 4, said collar 5 acting as a retainer for expandable element 6. Spring-like expandable element 6 prior to deployment is retained between the back end of the balloon 4a and the collar 5. Opening 3 is used for introduction of medication or blood as needed. FIG. 2 shows the inflatable balloon 4 fully inflated within the afflicted part of the blood vessel 7 where plaque 8 is compressed against the wall of the vessel 7 by the increased diameter of said balloon 4. Spring-like expandable element 6 is still in a compressed condition. FIG. 3 illustrates the dilatation balloon 4 deflated AND evacuated to create a diameter less then that of the expandable spring element 6 said smaller diameter allowing the spring element 6 to expand over the evacuated balloon 4 to its natural full length thereby providing radial support for the afflicted part of the vessel and preventing the now compressed plaque 8 from ever reclosing again. The fully expanded spring element 6 now becomes a liner for the afflicted vessel and the catheter can be withdrawn leaving the liner 6 permanently implanted preventing future restenosis.

Figure 4:
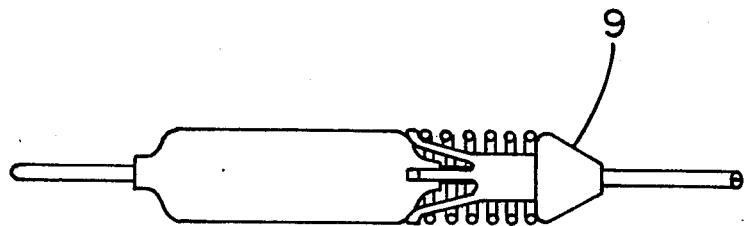
FIG. 4 shows an alternate method of retention and latching of the expandable spring like liner in its compressed condition.

The now implanted liner 6 being made of suitable metal, stainless steel or gold also allows for X-ray localization both during deployment and for post-operative periodic flouroscopic or X-ray inspection and evaluation. FIG. 4 shows an alternate means of retention for the expandable spring element 6. This design shows a one-piece retainer and latch combination 9 which at one end is fastened to the support hose 1 and the other end, the latching part of this retainer 9 rests on the back end portion of the balloon 4. It is the diameter of the inflatable balloon 4 which determines if the expandable element 6 is compressed and latched or unlatched and fully expanded. Other possible latching means based on the effective diameter of the inflatable balloon are not excluded to those skilled in the art without departing from the essence of this invention.

I claim:

1. In combination, a balloon catheter and spring prosthesis for insertion into an obstructed blood vessel comprising:
   an inflatable balloon adapted to dilate the blood vessel at the site of the obstruction, an inflation hose in fluid communication with said balloon to supply fluid to said balloon,
   an abutment fixed to said hose at a location spaced from said balloon,
   a longitudinally expandible helical spring prosthesis surrounding said hose and compressed and retained between said abutment and said balloon when at least partially inflated,
   said spring prosthesis being able to expand longtitudinally over said balloon when deflated and left in place in said blood vessel after said catheter is removed.

2. The combination as defined in claim 1 and also including a radially movable multipronged latch attached to said abutment, resting on the proximal end of said balloon and retaining the distal end of said spring prosthesis, said multiprong latch being radially collapsable as said balloon collapse to release said spring prosthesis.

* * * * *